United States Patent
Tang et al.

(10) Patent No.: US 8,916,734 B2
(45) Date of Patent: Dec. 23, 2014

(54) USING METHANESULFONYL HALIDE AS A KEY INTERMEDIATE FOR METHANE GAS TO LIQUID CONVERSION AND RAW COMMODITY CHEMICAL GENERATION

(75) Inventors: Yongchun Tang, Walnut, CA (US); Wei Zhou, Fremont, CA (US)

(73) Assignee: Sheeta Global Tech Corp., Covina, CA (US)

( * ) Notice: Subject to any disclaimer, the term of this patent is extended or adjusted under 35 U.S.C. 154(b) by 427 days.

(21) Appl. No.: 13/279,098

(22) Filed: Oct. 21, 2011

(65) Prior Publication Data

US 2012/0101311 A1   Apr. 26, 2012

Related U.S. Application Data

(60) Provisional application No. 61/455,432, filed on Oct. 21, 2010, provisional application No. 61/510,941, filed on Jul. 22, 2011.

(51) Int. Cl.
| | | |
|---|---|---|
| *C07C 17/093* | (2006.01) | |
| *C07C 309/00* | (2006.01) | |
| *C01B 7/04* | (2006.01) | |
| *C07C 303/10* | (2006.01) | |
| *C07C 17/35* | (2006.01) | |
| *C01B 7/03* | (2006.01) | |

(52) U.S. Cl.
CPC . *C07C 17/35* (2013.01); *C01B 7/04* (2013.01); *C07C 303/10* (2013.01); *C01B 7/035* (2013.01)
USPC .......................................... 570/253; 562/829

(58) Field of Classification Search
CPC ...... C07C 303/10; C07C 17/35; C07C 19/03; C07C 309/80; C01B 17/035
USPC .......................................... 570/253; 562/829
See application file for complete search history.

(56) References Cited

U.S. PATENT DOCUMENTS

| | | | |
|---|---|---|---|
| 4,997,535 | A | 3/1991 | Tatsumi et al. |
| 5,336,825 | A | 8/1994 | Choudhary et al. |
| 6,045,664 | A | 4/2000 | Ollivier |
| 8,278,493 | B2 | 10/2012 | Lorkovic |
| 8,519,202 | B2 | 8/2013 | Hirsekorn |
| 2008/0275279 | A1 | 11/2008 | Podkolzin et al. |
| 2011/0201841 | A1 | 8/2011 | Bowman et al. |
| 2012/0116121 | A1 | 5/2012 | Hirsekorn et al. |

FOREIGN PATENT DOCUMENTS

WO            9703952 A1    2/1997

OTHER PUBLICATIONS

Boeseken et al., the dissociation of methyl and ethyl sulfonyl chloride by aluminum chloride, Chemical Abstract, Document No. 9:8699, year 1914.*
Mukhopadhyay, S. et al.; Synthesis of methanesulfonyl chloride (MSC) from methane and sulfuryl chloride; Chem. Commun.; 2004; pp. 472-473; Royal Society of Chemistry.
Material Safety Data Sheet: Methanesulfonyl chloride (# 28050); 2009 (revision #5 date); Acros Organics BVBA.
Material Safety Data Sheet: Methane Sulfonyl Chloride; 2005 (revision #8 date); Arkema Inc.
Material Safety Data Sheet; Methanesulfonyl Chloride, 99.5% (gc) (ACC# 28050); 2005 (revision #3 date); Acros Organics N.V. via Fisher Scientific.
Dorsey, A. & Dewoskin, R.; Toxicological Profile for Chloromethane; Agency for Toxic Substances and Disease Registry; 1998; pp. 1-22; U.S. Department of Health and Human Services.
Addendum to the Toxicological Profile for Chloromethane; Agency for Toxic Substances and Disease Registry—Division of Toxicology and Environmental Medicine; 2009; Atlanta,GA.
Heldebrant, D. et al.; A reversible zwitterionic SO2-binding organic liquid; Energy & Environmental Science; 2010; pp. 111-113; Royal Society of Chemistry.
Treger, Y. et al.; Catalytic pyrolysis of methyl chloride for ethylene and propylene production; Catalysis in Industry, vol. 1, No. 2; 2009; pp. 117-120; Pleiades Publishing.
Fernandes, D. et al.; Catalytic conversion of chloromethane to methanol and dimethyl ether over metal-exchanged zeolite Y; Applied Catalysis A: General 367; 2009; pp. 108-112; ScienceDirect.
Khaleel, A. et al.; Catalytic conversion of chloromethane to methanol and dimethyl ether over mesoporous γ-alumina; Fuel Processing Technology 92; 2011; 1783-89; ScienceDirect.
Hibi, T. et al.; Catalysis by heteropoly compounds x. Synthesis of lower olefins . . . ; Applied Catalysis, 24; 1986; 69-83; Elsevier Science Publishers B.V.
Jaumain, D. & Su, B.; Direct catalytic conversion of chloromethane to higher hydrocarbons . . . ; Journal of Molecular Catalysis A: Chemical 197; 2003; 263-73; Elsevier.
Dorsey, A. & Dewoskin, R.; Toxicological Profile for Chloromethane; Agency for Toxic Substances and Disease Registry; 1998; pp. 149-156; U.S. Department of Health and Human Services.

* cited by examiner

*Primary Examiner* — Jafar Parsa
(74) *Attorney, Agent, or Firm* — Panqing He

(57) ABSTRACT for Processes for converting a methane or a methane containing natural gas to a monohalogenated methane and other downstream basic commodity chemicals going through methanesulfonyl halide as a key intermediate, whereby following its formation, the methanesulfonyl halide is allowed to decompose under a substantially anhydrous condition, preferably in the presence of a catalyst complex, and whereby in addition to the monohalogenated halide, a hydrogen halide and a sulfur dioxide are also formed in the overall conversion, both of which may be recycled back to the beginning of the processes. Additionally, compositions utilizing such a key intermediate for the same purposes are also disclosed.

12 Claims, 4 Drawing Sheets

Figure 1:
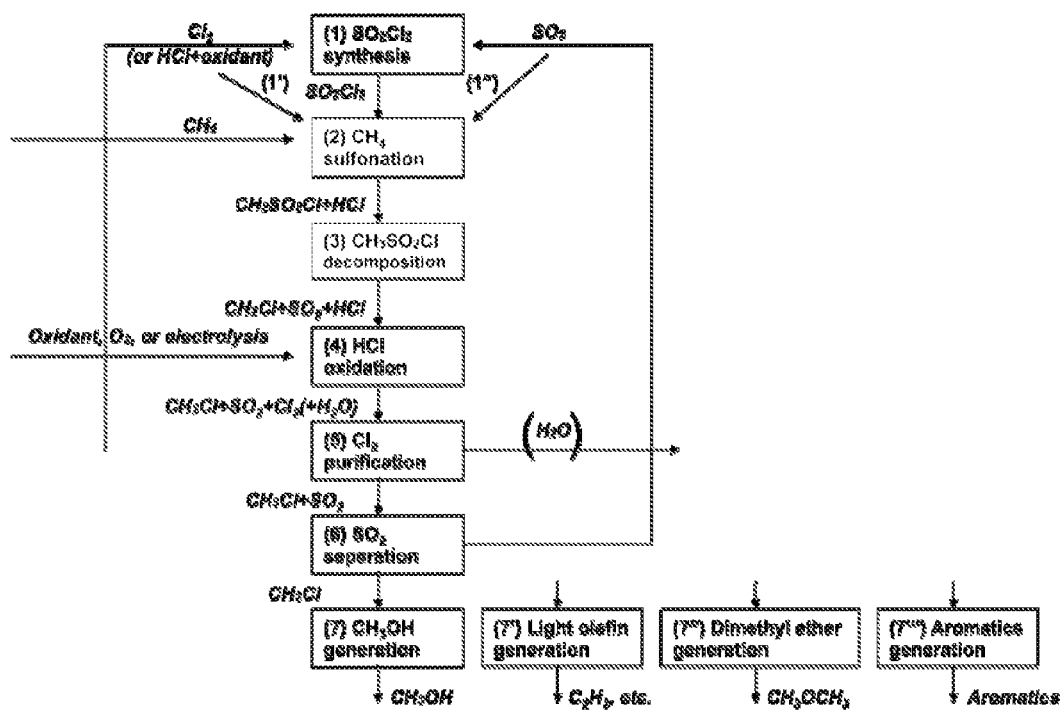

USING METHANESULFONYL HALIDE AS A KEY INTERMEDIATE FOR METHANE GAS TO LIQUID CONVERSION AND RAW COMMODITY CHEMICAL GENERATION

CROSS-REFERENCE TO RELATED APPLICATIONS

This application claims the benefit of U.S. Provisional Application No. 61/455,432, filed Oct. 21, 2010, and U.S. Provisional Application No. 61/510,941, filed Jul. 22, 2011.

BACKGROUND OF THE INVENTION

Methane from natural gas is an important raw material. North America alone has an estimated 1160 trillion cubic feet (tcf) of proven natural gas reserves. If captured and converted, the gas would, after conversion losses, enable 250 billion barrels of synthetics, which can be used from clean-burning diesel to jet fuel. Yet current high-temperature hydrocarbon conversion technologies are expensive and inefficient. Therefore, there is a need for low-temperature gas to liquid (LT-GTL) technologies. Another important challenge is that of the estimated 6600 tcf worldwide natural gas proven reserves, some 30%-60% are classified as stranded gas, i.e., gas that has been discovered but remain unusable for either physical or economic reasons.

The need to capture and utilize natural gas resources efficiently as an alternative chemical feedstock is becoming more urgent due to diminishing proven reserves and increasing consumption of crude oil. These trends are reflected in the expectation that unconventional gas production will grow significantly. Although establishing skid-mounted LT direct hydrocarbon conversion technology to capture existing reserves fully and efficiently has been a top priority, it has been met with the two challenges described above.

Returning to examine these challenges in some detail in reverse order, it is noted first there are geographic barriers to exploiting stranded gas economically. In geographically remote locations, pipeline infrastructure is lacking. Also, although there is gas associated with crude oil production operations, the quantities are often sub-economic to permit transport to market. Additionally, from offshore deepwater oil production, gas is produced that is difficult to capture. Second, the current dominant GTL technology is energy-intensive, requiring operations at temperatures generally greater than 700 C; capital-intensive, as expensive metal oxidants are required; and technically lacking, giving low conversion and carbon selectivity rates, the latter being 60% maximum.

These barriers have negative economic and environmental consequences. The former include an inability to tap vast reserves of stranded gas, high capital costs that amount to greater than 40% of production costs, and prevention of small- and middle-scale gas exploration. While among pollution concerns are the fact that the majority of explored gas is flared, creating greenhouse effects, and that current processes have low carbon efficiency. Offshore associated gas poses a special set of challenges, where skid-mounted GTL technology does not exist, production rates fluctuate, production volume is sub-economic, and high capital expenditures are required for gas capture and export. As a result, 150 billion cubic meter of gas is flared per year, equivalent to about 25% of the US's or 30% of the EU's gas consumption, per year.

Focusing on the technical aspects of the current GTL technology, one notes that methanol production via synthesis gas generation is the dominant technology in the natural gas market. As the major species in natural gas, methane's carbon-hydrogen bond has a high bond energy of 439 kJ/mol, and as a result is extremely insert to reactivity. In the dominant current approach, methane is oxidized in an early step at 700 C-1000 C to produce a gas mixture of carbon monoxide and hydrogen, known as synthesis gas or syngas, which is further catalytically converted to methanol. Methanol is then used as a major feedstock to make formaldehyde, acetic acid, methyl chloride, olefins, gasoline additives, and other chemicals and products. Methanol can also be used directly as a fuel for vehicles. However, the dominant current approach calls for high temperatures and is therefore expensive to operate. It also has many steps in the process and requires high capital expenditure. As well, there is no skid-mounted plant that is currently economically applicable or feasible.

Attempts have been made to improve the natural gas GTL process in the past decades. One line of research has been to use methane to produce monohalogenated methane, which can then be further processed. GRT Incorporated, a US company located in Santa Barbara, for example, has developed a novel, fundamentally simpler, and more direct approach to GTL processes, whereby rather than first generating synthesis gas from methane, methane is activated by bromine ($Br_2$), reaction being captured by the following Equation (1):

$$CH_4 + Br_2 \rightarrow CH_3Br + CH_2Br_2 + CHBr_3 \quad (1)$$

By eliminating the need to form synthesis gas, the GRT process is more economically applicable to biomethane and to natural gas from small- and medium-size stranded gas fields. Dow Chemical also developed a technology to convert methane to methyl chloride, and again di- and tri-chloromethanes are major products in the product mixture. Their technology may be shown as follows by Equation (2):

$$CH_4 + Cl_2 \rightarrow CH_3Cl + CH_2Cl_2 + CHCl_3 + HCl \quad (2)$$

The main difficulty of both improved approaches is carbon selectivity. That is, while a monohalogenated product would be most desirable, reactions in both cases do not stop at the monohalogenated methane product, but instead proceed to allow polyhalogenated products as major species in the product mixture. Because additional separation steps are economically unattractive, there is a need to develop methods of producing methyl halide without unwanted byproducts.

Other references in the art teach processes to halogenate methane. For example, U.S. patent application Ser. No. 11/912,376 describes an oxidative halogenation process for preparing a halogenated $C_1$ product by contacting methane or a $C_1$ halogenated hydrocarbon with a source of oxygen, a source of halogen, and a catalyst, at specific molar ratios of reactant hydrocarbon to oxygen and/or halogen. (The same reference, incidentally, points to a long sought need in the art for a solution to convert natural gas to useful chemical feedstocks, echoing the description provided above.) U.S. patent application Ser. No. 13/123,908 describes another process to oxidatively halogenate methane, by placing a feedstream that comprises methane, a source of halogen, a source of oxygen, and a source of diluents gas in contact with a first and then a second catalyst.

The '376 application, however, describes a process that requires a high temperature for the reaction to occur, listing a general range that is greater than about 375 C and less than about 700, and is relatively cumbersome to use. The '908 application also describes an involved process that requires operation at higher temperatures (at a range of 200 C to 600 C) in at least one step in the process, does not offer great selectivity for the monohalogenated species, and produces several impurities, including carbon monoxide. The '908 application additionally produces water and hydrogen chloride, which as taught by the '376 application will allow formation of an azeotrope from which it is difficult and expensive to separate dry hydrogen chloride for recycling purposes.

Moreover, neither process specifies the appearance of methanesulfonyl halogen or methanesulfonyl chloride in the reaction process or their use as reaction intermediates.

Methanesulfonyl chloride (MSC), a liquid at room temperature (boiling point=161 C), is a compound that methane can react with to form according to Equation (3):

$$CH_4 + SO_2Cl_2 \text{--(Urea-}H_2O_2\text{,RhCl}_3\text{,60 C,12 h,}H_2SO_4 \text{ solvent)--} > CH_3SO_2Cl + HCl \quad (3)$$

Although a versatile reagent that has several uses, among them as a mesyl group introduction species, a synthetic intermediate for photographic chemicals and agrochemicals, a stabilizer or catalyst, and a precursor to methanesulfonic acid (Mukhopadhyay et al., Chemical Communications, pp. 472-473 (2004), incorporated herein by reference), MSC's commercial market remains quite limited compared to such basic chemicals as for example methanol, light olefins, and dimethyl ether.

Further, because MSC is highly toxic, moisture sensitive, corrosive, and a lachrymator, it has not been thought of by previous references in the art as a compound that can serve as a key intermediate for methane conversion into useful chemicals, although it can be formed from methane. For example, U.S. Pat. No. 4,997,535 teaches a process to manufacture MSC from a mixture of methane, SO2 gas, and Cl2 gas under irradiation of light with wavelengths of 200~600 nm, and U.S. Pat. No. 6,045,664 describes a method to produce MSC by photo-chemical reaction of $CH_4$ with $Cl_2$ and $SO_2$, during which process a small amount of chlorinated methane in the form of a byproduct (less than 1%) was observed. Neither of these references describes useful thermal decomposition products of MSC, and in particular does not mention methyl chloride or chloromethane.

Additional references for the thermal decomposition products of methanesulfonyl chloride, as provided by the MSDS from three of the largest chemical providers are listed in completion as follows. (1) Acros Organics MSDS: hydrogen chloride, carbon monoxide, oxides of sulfur (SOx), carbon dioxide; (2) Arkema Inc. (which supplies Sigma-Aldrich) MSDS: methansulfonic acid (CH3SO3H), sulfur oxides (SOx), and carbon oxides (COx); and (3) Fisher Scientific MSDS: hydrogen chloride, carbon monoxide, oxides of sulfur, carbon dioxide. It is noted that methyl chloride does not appear among the listed thermal decomposition products of methanesulfonyl chloride.

Methyl chloride, a monohalogenated methane species that has been sought after in the art as a relatively pure reaction product, however, is an important commodity chemical. According to the 1998 "Toxicological Profile for Chloromethane" published by the Agency for Toxic Substances and Disease Registry of the U.S. Department of Health and Human Services, and its 2009 addendum, there are two common large-scale industrial methods to produce chloromethane or methyl chloride: methanol-HCl and methane chlorination. In the methane chlorination process, after HCl removal, a fractional distillation step is necessary to separate the four chlorinated methanes and isolate the mono-chlorinated product.

The same sources gave the US production amount in 1995 to be around 920 million ponds (417.3 million kg). As of 1998, there were at least 96 facilities in the U.S. that produced chloromethane, of which seven had production capacities in excess of 50 million ponds per year. At three of these, all the chloromethane generated were used on-site in silicone production, while at the other four, a large percentage of the output were also used on-site as feedstocks in the manufacture of other chemicals and products. Overall, chloromethane as of 1995 was used mainly (72%) in the production of silicones. Chloromethane has also been used in the production of agricultural chemicals (8%), methyl cellulose (6%), quaternary amines (5%), butyl rubber (3%), and for miscellaneous uses including tetramethyl lead (2%).

Therefore one sees that regarding methyl chloride, (1) one of the two processes for its production in large-scale current use employs methane as a reactant, but requires distillation to separate out the mono-chlorinated species; and (2) its feedstock use is of significance.

SUMMARY OF THE INVENTION

The process of the present invention couples the formation of a methanesulfonyl halide (MSH) to its thermal decomposition, exploiting MSH as a key intermediate in the process. While the thermal decomposition of MSH under specific conditions to give methyl halide was unexpected, the formation of MSH uses technologies described in the art. From the coupling as a whole, nevertheless, is derived a novel process. The term "under specific conditions" refers to carrying out the decomposition under a substantially anhydrous condition, and preferably in the presence of a catalyst complex. Also preferably the MSH is methanesulfonyl chloride (MSC). Using the chlorinated compounds for illustration, the coupled steps of the process of the current invention are as in Equations (4) (noting that formation of MSC from methane may be by other means not shown):

Intermediate formation: $CH_4 + SO_2Cl_2 \text{---} > CH_3SO_2Cl + HCl$ (4a)

Intermediate decomposition: $CH_3SO_2Cl \text{---(via condition/catalyst)---} > CH_3Cl + SO_2$ (4b)

Were it not for the unexpected decomposition step, the MSH formation step in this coupling would be of limited use, besides being already known in the art. Nevertheless, the MSH formation step plays an essential role for the whole, coupled process, as it enables the use of an abundant starting material, namely methane or a methane containing gas, large quantities of which are today wasted or stranded due to geographic and technical barriers, the latter of which the present whole coupled process surmounts in a novel and unexpected way.

Additionally, the entire coupled process not only produces, from methane or methane containing gas via MSH/MSC, methyl halide and preferably methyl chloride, a starting material needed in large quantities and especially useful in the production of silicones, but also allows the production of a number of other basic commodity or feedstock chemicals derived from methyl chloride or methyl halide, such as methanol, light olefins, dimethyl ether, and aromatics.

A particularly advantageous feature of the several aspects of the process is that a monohalogenated methane is produced as virtually the only halogenated methane product from the whole coupled process, considerably facilitating downstream chemical production. Additionally, the rate of conversion of the MSH intermediate to products is high, regularly exceeding 90% for several preferred embodiments. A further advantage of the several aspects of the present process is the very mild conditions under which they can be carried out, when compared to previous technologies. A catalytic temperature less than about 150 C for the key intermediate decomposition step is regularly achieved for preferred embodiments. Yet another advantage of the several aspects lies in their ease of operation or manufacture. The relatively mild conditions needed and the ease of operation for the several aspects, which by implication mean a lowering of cost, can go some ways towards meeting the existing need in the art, opening the door to on-site processing of methane and methane containing gas to produce methyl halide and other valuable feedstock chemicals at stranded gas sites.

These and other advantages of one or more aspects will become more apparent from considering the ensuing description and accompanying drawings.

BRIEF DESCRIPTIONS OF THE DRAWINGS

FIG. 1: A pathway from methane to methyl chloride and other commodity chemicals via methanesulfonyl chloride.

Figure 2:
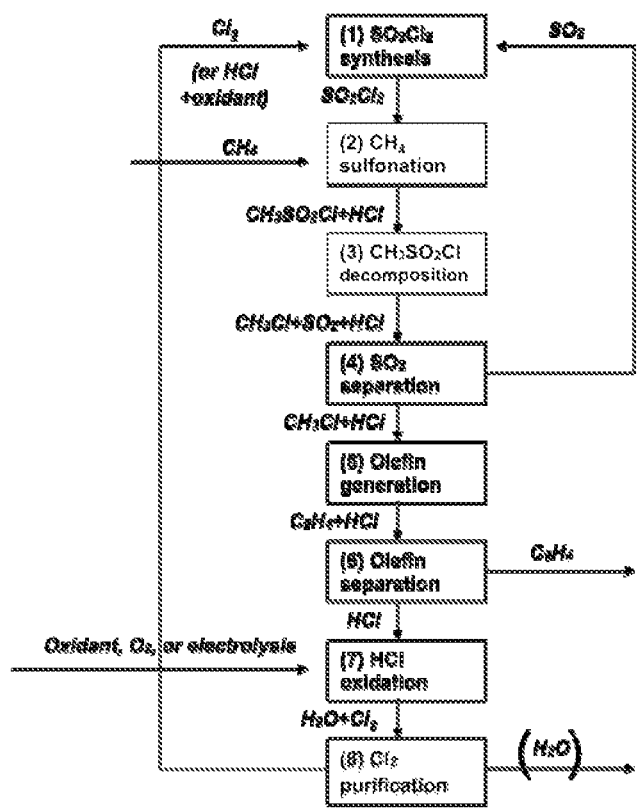

FIG. 2: A differently ordered route from methane to methyl chloride and olefins via methanesulfonyl chloride.

Figure 3A:
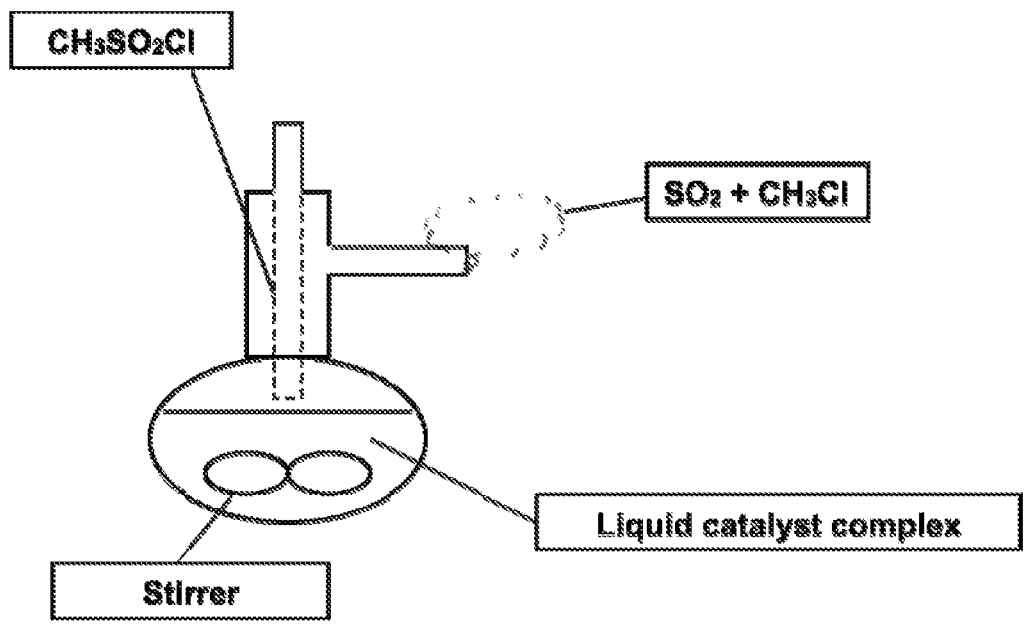

FIG. 3a: The methanesulfonyl chloride intermediate thermally decomposes in a composition via a liquid catalyst complex.

Figure 3B:
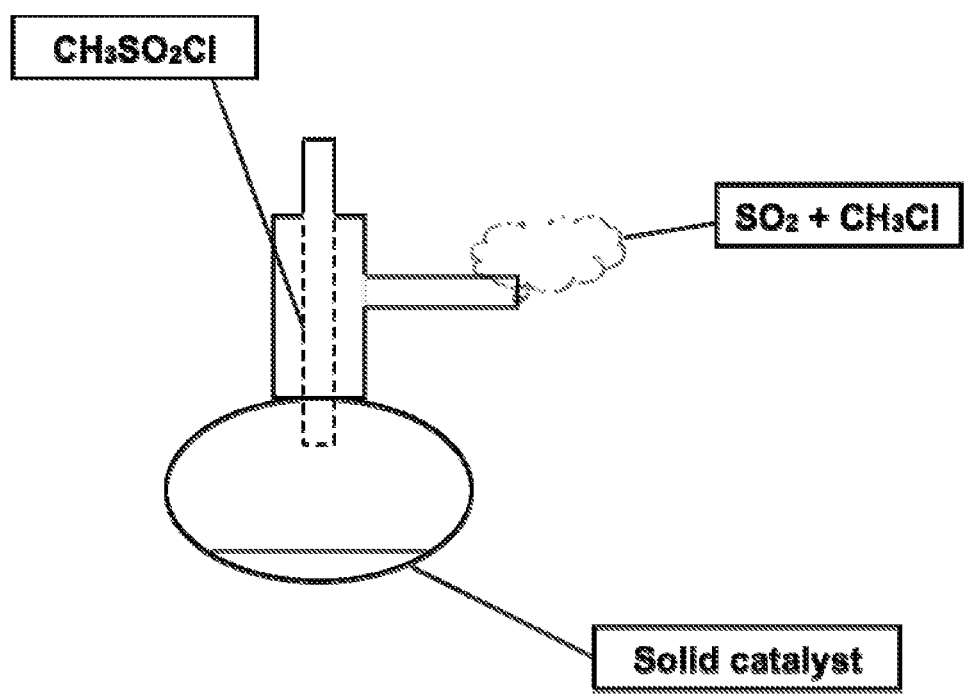

FIG. 3b: The methanesulfonyl chloride intermediate thermally decomposes in a composition via a solid catalyst complex.

DETAILED DESCRIPTION OF THE INVENTION

The process of the present invention couples the formation of a methanesulfonyl halide (abbreviated MSH) to its thermal decomposition, exploiting MSH as a key intermediate in the process.

As shown in FIG. 1, steps 2 and 3, an aspect of the process converts a methane or a methane containing natural gas to a monohalogenated methane; the process proceeds or goes through the MSH as an intermediate, whereby following its formation, the MSH is allowed to decompose under a substantially anhydrous condition, preferably in the presence of a catalyst complex, and whereby, in addition to the monohalogenated methane, a hydrogen halide and a sulfur dioxide are also formed in the overall conversion and decomposition process.

As shown in FIG. 1, steps 1-3, in another aspect, the present process produces a monohalogenated methane from a methane or a methane containing natural gas through a MSH as an intermediate, whereby the process comprises the steps of reacting the methane with a sulfur dioxide and a halogen, with the sulfur dioxide, a hydrogen halide, and an oxidant, or with a sulfuryl halide, to form the MSH intermediate and a hydrogen halide; and contacting the MSH with a catalyst complex to form the monohalogenated methane and a sulfur dioxide under a reaction condition that is substantially anhydrous. The term "oxidant" used herein refers to a solid that is capable of oxidizing the hydrogen halide to form halogen gas under temperature conditions from about 25 C to about 400 C.

As shown in FIG. 1, steps 1, 1', and 1", in preferred embodiments of the process that converts a methane or a methane containing gas to a monohalogenated methane, the formation of MSH may be accomplished by the methane first reacting with a sulfur dioxide and a halogen; a sulfur dioxide, a hydrogen halide, and an oxidant, preferably one that can oxidize the hydrogen halide to the halogen; or a sulfuryl halide directly.

In one preferred embodiment, the catalyst complex used in the process converting a methane or a methane containing natural gas to a monohalogenated methane comprises a Lewis acid, a nitrogen-containing base, or both.

In an alternatively preferred embodiment, the catalyst complex used in the process producing a monohalogenated methane through a MSH as an intermediate comprises a Lewis acid, a nitrogen-containing base, or both. In another alternatively preferred embodiment of such production, the catalyst complex used comprises a Lewis acid. In yet another alternatively preferred embodiment of such production, the catalyst complex used comprises a nitrogen-containing base.

In a preferred embodiment of the process producing a monohalogenated methane, the catalyst complex is at least one of an ionic liquid, a Lewis acid, or a nitrogen containing base. Ionic liquids generally have bulky cations, including asymmetric quaternary ammonium, quaternary phosphonium, and sulfonium types, or heteroaromatics such as 1,3-dialkylimidazolim, all having low symmetry, weak intermolecular interactions, and low charge densities; they can also be of the haloaluminate variety, exemplified by $AlCl_3$-1-(1-butyl)pyridiniumchloride ($AlCl_3$-BupyCl); other examples of ionic liquid cations include pyrrolidinium, pyrrolium, isoquinolium, and pyrimidine-based fused ring cations. The nitrogen containing base can be a heterocyclic nitrogen base, also called a heterocyclic amine, which is often a conjugate base of the cation of many ionic liquid species. The ionic liquid used for the invention disclosed herein is at least one of a compound comprising a cation selected from the group consisting of imidazolium, a substituted imidazolium, pyrazolium, a substituted pyrazolium, pyridinium, a substituted pyridinium, pyrazinium, a substituted pyrazinium, a 1,2,4-triazolium, a substituted 1,2,4-triazolium, a quaternary ammonium cation, and mixtures thereof; or a haloaluminate ionic liquid. In an alternative preferred embodiment of the process producing a monohalogenated methane, the catalyst complex comprises a Lewis acid selected from the group consisting of an aluminum halide, a boron trihalide, an acidic zeolite, and mixtures thereof. Lewis acidic zeolites, an example of which is ZSM-5, are those that provide aprotonic Lewis sites, arising from charge compensating cations or extra-framework aluminum atoms, with which a (Lewis) base molecule can form an adduct. In another preferred embodiment of the process producing a monohalogenated methane, the catalyst complex comprises a nitrogen-containing base selected from the group consisting of imidazole, a substituted imidazole, pyrazine, a substituted pyrazine, an imidazoline, a substituted imidazoline, pyridine, a substituted pyridine, and mixtures thereof.

As shown in FIG. 1, steps 1-5 and FIG. 2, steps 1, 7, and 8, a halogen (preferably chlorine) is needed to react with methane or methane containing gas in certain preferred embodiments of the process producing a monohalogenated methane. Thus in such embodiments, the hydrogen halide (preferably hydrogen chloride) that is always formed along with the MSH (or preferably the MSC) intermediate may be separated and set aside for other uses, or allowed to undergo without separation a further process comprising oxidizing the hydrogen halide to a halogen by contacting it with an oxidant or a source of oxygen or by electrolysis; obtaining the halogen as part of a product stream comprising unreacted hydrogen halide, methane, MSH (or preferably MSC), monohalogenated methane, and sulfur dioxide, and possibly additionally water; separating the halogen from the product stream, resulting in a recycled halogen stream comprising substantially of the halogen (preferably chlorine); and recycling the recycled halogen stream directly to the beginning of the monohalogenated methane production process to react with methane. The term "comprising substantially of the halogen" is herein used to refer to the product stream that currently is felt should typically contain greater than about 95 mole percent, and more preferably greater than about 98 mole percent, halogen. The hydrogen halide (preferably hydrogen chloride) that is separated and set aside can, but need not, also undergo the same further process and be recycled in the said manner. The alternate production route as shown in FIG. 2, contrasted with that shown in FIG. 1, additionally demonstrates that the halogen need not be immediately purified as it is generated from hydrogen halide.

In several embodiments of the monohalogenated methane production process, sulfur dioxide is consumed and then produced, respectively, during the formation of MSH and its decomposition. This is shown in FIG. 1, steps 1, 5 and 6; FIG. 2, steps 1, 3, and 4. Therefore, in such embodiments, the sulfur dioxide formed, being obtained as a constituent of a product stream comprising methane, methanesulfonyl halide, monohalogenated methane, and hydrogen halide, can be recovered for later use or recycled, and if recycled is through a process comprising separating the sulfur dioxide from the product stream, resulting in a recycle stream comprising substantially of the sulfur dioxide, and recycling the recycle stream directly to the beginning of the monohalogenated methane production process. The term "comprising substantially of the sulfur dioxide" is herein used to refer to the product stream described in the instant paragraph that currently is felt should typically contain greater than about 90 mole percent, and more preferably greater than about 95 mole percent, sulfur dioxide or sulfuric acid. WO 9,703,952 and Heldebrant, D. et al., Energy & Environmental Science, Vol. 3 pp. 111-113 (2010) teach methods that may be used to perform the initial separation of sulfur dioxide from the product stream.

In a preferred embodiment of the monohalogenated methane production process through a MSH as an intermediate, the monohalogenated halogen is methyl chloride (abbreviated MSC), the halogen is chlorine, the halogen halide is hydrogen chloride, and the sulfuryl halide is sulfuryl chloride. FIG. 1 and the examples later illustrate using these chlorinated forms.

As shown in FIG. 1, 7-7''', in other preferred embodiments of the monohalogenated methane production process through a MSH as an intermediate, the methyl chloride produced, either as it is being formed or first recovered, is optionally employed in a downstream process to prepare methanol, dimethyl ether, a light olefin, or an aromatic compound. Processes and methods for such downstream preparations are known in the art. For example, Treger, Y. et al. disclose the conversion of methyl chloride to light olefins, particularly ethylene and propylene, by a zeolite catalyst and silicoaluminumophosphate, which catalytic activity can be regenerated after loss, resulting in a selectivity for ethylene plus propylene of 80-85% (see, Catalysis in Industry, Vol. 1, pp. 117-120 (2009)).

In yet other references in the art, methods that convert methyl chloride to methanol and dimethyl ether over metal-exchanged zeolite Y or mesoporous gamma-alumina, for example, are disclosed (see, Fernandes, D., et al., Applied Catalysis A: General, Vol. 367, pp. 108-112 (2009) and Khaleel, A. et al., Fuel Processing Technology, Vol. 92, pp. 1783-1789 (2011)). Should methyl chloride be first converted to methanol and dimethyl ether, Hibi, T. et al. describe methods that convert methanol and dimethyl ether into hydrocarbons over several salts of 12-tungstophosphoric acid, H3PW12O40, at 563 K by a flow method (see, Applied Catalysis, Vol. 24, pp. 69-83 (1986)).

In yet further references in the art, for example U.S. Pat. No. 5,336,825 and Jaumain and Su, Journal of Molecular Catalysis A: Chemical, Vol 197, pp. 263-273 (2003), methods that use among other catalytic materials, ZSM-5 exchanged with alkali cations, to convert chloromethane to aromatics are taught. The aforementioned citations in this and the two preceding paragraphs are incorporated herein by reference. Although the downstream preparations in isolation are known in the art, the whole, entire process of producing methanol, dimethyl ether, light olefins, or aromatics, starting from methane or a methane containing gas and proceeding through an MSH or MSC intermediate, is novel and quite unexpected. For an illustration of the entire path, see for example FIG. 1, steps 1-7 or steps 1-7'.

In yet another aspect, the invention utilizing MSH as a key intermediate is directed to a composition that comprises a methane or a methane containing gas; and a sulfur dioxide and a halogen, the sulfur dioxide, a hydrogen halide, and an oxidant, or a sulfuryl halide, whereby the methane reacts with the other species under a substantially anhydrous condition to form a monohalogenated methane, a hydrogen halide, and a sulfur dioxide, via a MSH intermediate, preferably in the of presence of a catalyst complex. An aspect or part of this composition is shown in FIG. 3a, where the methanesulfonyl chloride intermediate being formed from nearer the top of a container housing the composition may approach the catalyst complex located nearer the bottom, and the sulfur dioxide and methyl chloride products may be collected from a side of the same container housing. FIG. 3b performs a similar illustration, but for a solid catalyst complex.

In a preferred embodiment, the catalyst complex in the composition comprises a Lewis acid, a nitrogen-containing base, or both, and more preferably the halogen is chlorine, the hydrogen halide is hydrogen chloride, the sulfuryl halide is sulfuryl chloride, and the monohalogenated methane is methyl chloride. In another preferred embodiment, the catalyst complex is at least one of an ionic liquid, a Lewis acid, or a nitrogen containing base. In yet another preferred embodiment, the catalyst complex in the composition comprises a nitrogen-containing base.

The term "methane containing gas" used herein refers to a gas that contains from about 1% to about 100% of methane, preferably from about 80% to about 100% of methane. Examples of methane containing gases include but are not limited to: (1) a natural gas; (2) coal gases, (3) a synthetic gas resulting from coal to methane processes; (4) a biogenic gas; and (5) methane rich gases from solid waste fermentation. In an aspect, a methane containing gas can play the same role as methane.

The term "substantially anhydrous" or "substantially anhydrous condition" used herein refers to a water content of less than 5% in the thermal decomposition of MSH, and preferably of less than 1%, either of which may be achieved by a drying process. It is currently felt to be preferable that the water content be managed to be much less about 20 ppm, or the catalyst complex may be in activated.

The term "decomposition temperature" or "contacting temperature" used herein refers to a temperature applied to the decomposition of MSH, or the temperature at which MSH contacts a catalyst complex during the decomposition or thermal decomposition of MSH. This temperature does not need to be applied until MSH is formed, but when applied as MSH decomposes or reacts in the presence of the catalyst complex, will ensure that the decomposition or reaction proceeds at rates associated with preferred embodiments. It is preferred that a decomposition temperature be between about 25 C and about 300 C. It is more preferred that the decomposition temperature be between about 80 C and 150 C. A preferred decomposition temperature may depend on the choice of the catalyst complex. For example, decomposition temperature for a reaction using 2 g of aluminum chloride was 190 C, while that for a reaction using 1 g 1-ethyl-3-methylimidazolium chloride was 120 C, giving very comparable conversion yields of methanesulfonyl chloride and percent selectivity (see examples 3 and 1). The adjustment and optimization of the decomposition temperature is within the skills of the ordinary artisan.

For the purposes of this invention, the term "selectivity" or "percent selectivity" used herein means carbon selectivity unless specified or obviously clear otherwise, and is defined as moles of the methyl halide produced divided by total moles of carbon contained in the product, whether or not normalized as a percentage. Selectivity (i.e., carbon selectivity) for the methyl halide (or the synonymous monohalogenated methane) produced by processes and compositions disclosed herein is usually greater than about 90%, and preferably greater than about 95%.

For the purposes of this invention, the term "conversion yield" or "conversion of methanesulfonyl chloride" or "rate of conversion" used herein refers to the mole percent of methanesulfonyl chloride out of the total starting amount that has undergone chemical change, such as thermal decomposition.

The term "halogenated methane product" used herein refers to a mono-, di-, tri-, or tetrahalogenated methane, and preferably, a mono-, di-, tri-, or tetrachlorinated methane. From the MSH intermediate, preferred embodiments of processes of this invention produce approximately the same mole percent of sulfur dioxide as the halogenated methane products, but of the halogenated methane products, the monohalogenated methane product predominate, more specifically to the extent of greater than about 95 mole percent (95%). In several examples that follow it is shown that in the case of the chlorinated methanes, preferred embodiments gave no detectable peaks via GCMS for any chlorinated methanes save for methyl chloride, starting from MSC. The GCMS system and the method employed were capable of separating and detecting the other chlorinated methanes and halogenated hydrocarbon species, if present.

The term "methanesulfonyl halide intermediate" or "MSH intermediate" used herein refers to the methanesulfonyl halide that is formed, along with hydrogen halide, when methane, itself or as a constituent of a methane containing gas, is reacted with sulfuryl halide, with sulfur dioxide and halogen, or with sulfur dioxide, hydrogen halide, and the oxidant, and is then reacted away or thermally decomposed substantially as the monohalogenated methane and sulfur dioxide are formed. The term "reacted away or thermally decomposed substantially" in the precedent sentence refers to methanesulfonyl halide intermediate being consumed or converted to other species at preferably greater than about 80%, more preferably greater than about 90% conversion rate.

Having generally described the present invention, the same will be better understood by reference to certain specific examples, which are set forth herein for the purposes of illustrating the processes and compositions of this invention; the examples however should not be construed as limiting the invention in any manner. In light of the disclosure herein, those of skill in the art will recognize alternative embodiments of the invention that fall within the scope of the claims.

Example 1

An Ionic Liquid Catalyst Catalyzes the MSH Decomposition to its Methyl Halide

Using 1-ethyl-3-methylimidazolium chloride (EMIM+ Cl−) as the catalyst, the production of $CH_3Cl$ from methanesulfonyl chloride decomposition was performed at 120 C under atmospheric pressure. $EMIM^+Cl^-$, which is a solid at room temperature, melts to liquid at temperature above about 80 C. For 1 g of $EMIM^+Cl^-$, methanesulfonyl chloride was fed to the reactor at a rate of 3.5 mL/h. A typical reaction was over within seconds. The space velocity was about 3.9 per hour. GCMS was employed for the online gas product composition analysis. Only $CH_3Cl$ and $SO_2$ peaks were observed in this analysis. Several measurements of the $CH_3Cl$ to $SO_2$ ratio are shown in the table below. The conversion of methanesulfonyl chloride, as determined by the drainage gas gathering method with a gas bag in water, gave a conversion yield of 90%.

|  | #1 | #2 | #3 | #4 | #5 |
|---|---|---|---|---|---|
| CH3Cl (%) | 50.31 | 49.12 | 49.24 | 49.09 | 49.55 |
| SO2 (%) | 49.69 | 50.88 | 50.76 | 50.91 | 50.45 |
| Ratio | 1.01 | 0.97 | 0.97 | 0.96 | 0.98 |
| % Selectivity for CH3Cl |  |  | ~100 |  |  |

Example 2

An Ionic Liquid Catalyst that is a Quaternary Ammonium Salt Catalyzes the MSH Decomposition to its Methyl Halide Using tetramethylammonium chloride, $N(CH_3)_4Cl$, as the catalyst, the decomposition of methanesulfonyl chloride was conducted at 130 C under atmosphere pressure. For 1 g of $N(CH_3)_4Cl$, methanesulfonyl chloride was fed to the reactor at a rate of 3.5 mL/h. A typical reaction was over within seconds. The space velocity was about 4.1 per hour. GCMS was employed for the online gas product composition analysis. Only $CH_3Cl$ and $SO_2$ peaks were observed in the GCMS analysis. Several measurements of the $CH_3Cl$ to $SO_2$ ratio are shown in the table below. The conversion of methanesulfonyl chloride, as determined by the drainage gas gathering method with a gas bag in water, gave a conversion yield of 93%.

|  | #1 | #2 | #3 | #4 | #5 |
|---|---|---|---|---|---|
| CH3Cl (%) | 49.73 | 49.62 | 48.39 | 48.25 | 48.15 |
| SO2 (%) | 50.27 | 50.38 | 51.61 | 51.75 | 51.85 |
| Ratio | 0.99 | 0.98 | 0.94 | 0.93 | 0.93 |
| % Selectivity for CH3Cl |  |  | ~100 |  |  |

Example 3

A Lewis Acid Catalyst that is an Aluminum Halide Catalyzes the MSH Decomposition to its Methyl Halide Using aluminum chloride, $AlCl_3$, as the catalyst, the production of $CH_3Cl$ from methanesulfonyl chloride decomposition was performed at 190 C under atmospheric pressure. For 2 g of $AlCl_3$, methanesulfonyl chloride was fed to the reactor at a rate of 3.5 mL/h. A typical reaction was over within seconds. The space velocity was about 3.1 per hour. GCMS was employed for the online gas product composition analysis. Only $CH_3Cl$ and $SO_2$ peaks were observed in the GCMS results. Several measurements of the $CH_3Cl$ to $SO_2$ ratio are shown in the table below. The conversion of methanesulfonyl chloride, as determined by the drainage gas gathering method with a gas bag in water, gave a conversion yield of 88%.

|  | #1 | #2 | #3 | #4 | #5 |
|---|---|---|---|---|---|
| CH3Cl (%) | 49.83 | 49.46 | 50.23 | 49.17 | 50.47 |
| SO2 (%) | 50.17 | 50.54 | 49.77 | 50.83 | 49.53 |
| Ratio | 0.99 | 0.98 | 1.01 | 0.97 | 1.02 |
| % Selectivity for CH3Cl |  |  | ~100 |  |  |

Example 4

A Nitrogen-Containing Base Catalyst, 1-Methylimidazole, Catalyzes the MSH Decomposition to its Methyl Halide Using 1 g of 1-methylimidazole as the catalyst and a source feeding rate of 4 mL/h, the decomposition of methanesulfonyl chloride was run at 100 C under atmospheric pressure. A typical reaction was over within seconds. The space velocity was calculated to be about 4.1 per hour. GCMS was employed for the online gas product composition analysis. Only $CH_3Cl$ and $SO_2$ peaks were observed in the GCMS analysis. Several measurements of the $CH_3Cl$ to $SO_2$ ratio are shown in the table below. The conversion of methanesulfonyl chloride, as determined by the drainage gas gathering method with a gas bag in water, gave a conversion yield of 97%.

|                      | #1    | #2    | #3    | #4    | #5    |
|----------------------|-------|-------|-------|-------|-------|
| CH3Cl (%)            | 49.81 | 49.42 | 50.36 | 51.57 | 49.56 |
| SO2 (%)              | 50.19 | 50.58 | 49.64 | 48.43 | 50.44 |
| Ratio                | 0.99  | 0.98  | 1.01  | 1.06  | 0.98  |
| % Selectivity for CH3Cl |    |       | ~100  |       |       |

Example 5

An Ionic Liquid Catalyst of a Haloaluminate Variety, an Aluminum Chloride/2-Methylpyrazine Hybrid, Catalyzes the MSH Decomposition to its Methyl Halide A hybrid catalyst prepared from aluminum chloride and 2-methylpyrazine was also tested in another experiment. 1 g of aluminum chloride was first dissolved in 3 g of 2-methyl pyrazine, which was then heated to 170 C to form a solid adduct product. The adduct product was then used to catalyze the decomposition of methanesulfonyl chloride at 170 C under atmospheric pressure. Methanesulfonyl chloride was fed to the reactor at a rate of 5 mL/h. A typical reaction was over within seconds. The space velocity was calculated to be about 1.44 per hour. GCMS was employed for the online gas product composition analysis. Only $CH_3Cl$ and $SO_2$ peaks were observed in the GCMS results. Several measurements of the $CH_3Cl$ to $SO_2$ ratio are shown in the table below. The conversion of methanesulfonyl chloride, as determined by the drainage gas gathering method with a gas bag in water, gave a conversion yield of 95%.

|                      | #1    | #2    | #3    | #4    | #5    |
|----------------------|-------|-------|-------|-------|-------|
| CH3Cl (%)            | 49.33 | 49.10 | 49.56 | 49.25 | 49.17 |
| SO2 (%)              | 50.67 | 50.90 | 50.44 | 50.75 | 50.83 |
| Ratio                | 0.97  | 0.96  | 0.98  | 0.97  | 0.97  |
| % Selectivity for CH3Cl |    |       | ~100  |       |       |

Papers and patents cited in the disclosure are expressly incorporated by reference in their entirety. It is to be understood that the description, specific examples, and figures, while indicating preferred embodiments, are given by way of illustration and exemplification and are not intended to limit the present invention. Various changes and modifications within the present invention will become apparent to the skilled artisan from the disclosure contained herein. Therefore, the spirit and scope of the appended claims should not be limited to the description of the preferred versions contained herein.

What is claimed is:

1. A process of converting a methane containing gas to a monohalogenated methane comprising traversing a reaction pathway wherein a methanesulfonyl halide is formed as an intermediate and decomposes under a substantially anhydrous condition, and wherein the methanesulfonyl halide decomposes in the presence of a catalyst complex that is at least one of an ionic liquid or a conjugate base of a nitrogen containing cation of said ionic liquid.

2. The process of claim 1 wherein the methanesulfonyl halide decomposes at a decomposition temperature between about 25 C and about 300 C.

3. The process of claim 1 wherein the methanesulfonyl halide decomposes at a decomposition temperature between about 80 C and about 150 C.

4. A process of producing a monohalogenated methane from a methane containing gas through a methanesulfonyl halide intermediate, comprising:
   a) reacting the gas to form the methanesulfonyl halide intermediate; and
   b) contacting the methanesulfonyl halide intermediate with a catalyst complex to form the monohalogenated methane under a reaction condition that is substantially anhydrous, wherein the catalyst complex is at least one of an ionic liquid or a conjugate base of a nitrogen containing cation of said ionic liquid.

5. The process of claim 4 wherein the catalyst complex is an ionic liquid.

6. The process of claim 5 wherein the ionic liquid is at least one of (a) a compound comprising a cation selected from the group consisting of imidazolium, a substituted imidazolium, pyrazolium, a substituted pyrazolium, pyridinium, a substituted pyridinium, pyrazinium, a substituted pyrazinium, a 1,2,4-triazolium, a substituted 1,2,4-triazolium, a quaternary ammonium cation, and mixtures thereof; or (b) a haloaluminate ionic liquid.

7. The process of claim 4 wherein the conjugate base of the nitrogen containing cation of said ionic liquid is selected from the group consisting of imidazole, a substituted imidazole, pyrazine, a substituted pyrazine, an imidazoline, a substituted imidazoline, pyridine, a substituted pyridine, and mixtures thereof.

8. The process of claim 4 wherein the methanesulfonyl halide contacts the catalyst complex at a contacting temperature between about 25 C and about 300 C.

9. The process of claim 4 wherein the methanesulfonyl halide contacts the catalyst complex at a contacting temperature between about 80 C and about 150 C.

10. The process of claim 4 wherein a selectivity for the monohalogenated methane is greater than about 90%.

11. The process of claim 4 wherein a selectivity for the monohalogenated methane is greater than about 95%.

12. The process of claim 4 wherein the monohalogenated methane constitutes greater than about 95% of all halogenated methane products.

* * * * *